US00PP07808P

United States Patent [19]

Fleming

[11] Patent Number: Plant 7,808

[45] Date of Patent: Feb. 25, 1992

[54] KALANCHOE PLANT NAMED SPARKLER

[75] Inventor: Margaret M. Fleming, Soquel, Calif.

[73] Assignee: The Plant Company, Soquel, Calif.

[21] Appl. No.: 606,844

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner

[57] ABSTRACT

A Kalanchoe plant named Sparkler particularly characterized by its bright, clear yellow flower color; flower diameter of up to 17 mm at maturity; flowering response of from 11 weeks in summer to 13 weeks in winter after start of short days; floriferous, with excellent display of many flowers; excellent keeping quality of both flowers and foliage; excellent free branching with or without pinching; intermediate vigor with short internodes and medium sized foliage; good response to B-9 to reduce peduncle elongation, and adaptability to various pot sizes.

2 Drawing Sheets

The present invention relates to a new and distinctive cultivar of Kalanchoe plant, botanically known as *Kalanchoe blossfeldiana* Poelln., and referred to by the cultivar name Sparkler.

Sparkler, identified as 579-328, is a product of a planned breeding program which had the objective of creating new Kalanchoe cultivars for year-round commercial production having an earlier flowering response, good branching yet compact flowering plants, suitability for flowering in pots ranging from 10 to 15 cm, and having good flower and foliage keeping quality.

Sparkler was originated by the inventor Margaret M. Fleming from a controlled selfing of the parent plant, an unnamed seedling identified as 402-087, produced from the crossing of Cinnabar and Fortyniner in Half Moon Bay, Calif., in 1984.

Sparkler was discovered and selected as one flowering plant within the progeny of the stated selfing by Margaret M. Fleming in February of 1986 in a controlled environment in Soquel, Calif.

The first act of asexual reproduction of Sparkler was accomplished when vegetative cuttings were taken from the initial selected in July 1986 in a controlled environment in Soquel, Calif., by Margaret M. Fleming.

Horticultural examination of controlled flowerings of successive plantings has shown that the unique combination of characteristics as herein disclosed for Sparkler are firmly fixed and are retained through successive generations of asexual reproduction. Sparkler has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Sparkler which, in combination, distinguish this Kalanchoe as a new and distinct cultivar:

1. Bright, clear yellow flower color.
2. Flower diameter of 15 to 17 mm at maturity.

3. Flowering response of from 11 weeks in summer to 13 weeks in winter after start of short days.
4. Floriferous, with excellent display of many flowers.
5. Excellent keeping quality of both flowers and foliage, with each floret lasting more than two weeks under normal conditions of finishing and holding.
6. Excellent free branching with or without pinching.
7. Intermediate vigor with short internodes and medium sized foliage.
8. Good responsiveness to B-9 to reduce peduncle elongation.
9. Proper scheduling makes this new cultivar suitable for production in 10 cm to 15 cm pots.

The accompanying colored photographic drawings show typical inflorescence and leaf characteristics of Sparkler, with colors being as nearly true as possible with illustrations of this type.

Sheet 1 is a color photograph of Sparkler grown as a non-pinched flowering Kalanchoe in a 10 cm pot.

Sheet 2 is a black and white photograph showing the leaves of Sparkler at three stages of development (mature, intermediate and immature).

In comparison to the material grandparent Fortyniner, both cultivars have yellow flower color, an 11-13 week flowering response, and are similar in vigor and habit. Sparkler and Fortyniner are distinctly different in the keeping qualities of the flowers and foliage, and in foliage color and other characteristics. Both the flowers and foliage of Sparkler are long keeping, while the flowers and foliage of Fortyniner are known for their short life. The foliage of Sparkler is a lighter green than the foliage of Fortyniner, and the leaves are larger, less fleshy, and more flexible than the leaves of Fortyniner. They are also more durable and less likely to degrade, with the foliage of Fortyniner having a tendency to crack when bent in sleeving or handling. Large cracks can of course result in losing all or part of the leaf. The leaves of Fortyniner are also subject to chlorosis of the tips, resulting in weakened tissue which is susceptible to secondary Botrytis which, when present, can spread to take over all the lower leaves of adjacent plants.

Sparkler may also be compared to the cultivar Goldstrike, disclosed in U.S. Plant Pat. No. 6,632. Sparkler and Goldstrike have a similar flowering response to short days, and are both in the generally yellow flower color category. However, the yellow flower color of Sparkler is a bright clear yellow, with no bronzing even when finished cool, while the more golden yellow of Goldstrike bronzes under those same finishing conditions. The flowers and foliage of Sparkler are also more long lasting than the flowers and foliage of Goldstrike. In addition, Sparkler is more vigorous in growth than Goldstrike, thus being more suitable for larger pots. Goldstrike is very compact, and is best suited for a 10 cm pot or smaller.

Sparkler can also be compared to the grandparent Cinnabar. The foliage color of both cultivars are similar, but the flowers of Sparkler are a clear yellow, as contrasted with the red/orange flowers of Cinnabar. A further difference is in the flowering response periods. Cinnabar has a very early flowering response of 9–11 weeks from thre start of short day treatment, as compared with the 11–13 weeks required for Sparkler. However, the flowers of Cinnabar fade rapidly, as contrasted to the flowers of Sparkler which are long lasting.

In the following description color references are made to The Royal Horticultural Society Colour Chart. The color values were determined on plant material grown as a non-pinched pot plant in a 10 cm pot in Soquel, Calif., on Aug. 10, 1988.

Classification:

*Botanical.*—*Kalanchoe blossfeldiana* Poelln. cv. Sparkler.

*Commercial.*—Flowering pot Kalanchoe.

Parentage:

(A) *Type cutting.*—Short tip cutting, with stems up to 2 cm.

(B) *Time to root.*—10 days at 21° C. in summer; 14 days at 21° C. in winter.

(C) *Rooting habit.*—Many very fine roots, fibrous.

Plant description:

(A) *Form.*—Moderately vigorous, upright growth. Growing and scheduling practices can produce a small plant in a 10 cm pot up to a larger plant in a 15 cm pot.

(B) *Habit of growth.*—Rate of growth vigorous for this type of plant. Generally, shoots are formed at every node, with internodes being 15–30 mm for a vegetative natural plant; height of plant above 10 cm pot approximately 20–30 cm, based on 3–4 applications of 3500 ppm B-9 SP growth regulator.

(C) *Foliage description.*—Leaves simple, opposite, slightly lobed. 1. Size: Average full grown leaf in a 10 cm flowering pot is 130 mm long×75 mm wide. 2. Shape: Ovate to elliptic, apex obtuse to slightly pointed, base attenuate. 3. Texture: Glabrous, coriaceous, succulent. 4. Margin: Sinuate to crenate. 5. Color (mature foliage): Upper surface 147A; under surface 147B. 6. Durability: Excellent; no degradation observed even on the lower foliage of plants retained for months beyond their normal life expectancy. The foliage of Sparkler is a great improvement over the foliage of the older yellow flowered varieties Fortyniner, Fujii, Goldstrike, and Yellow Nugget. 7. Foliar diseases: Resistant or immune to Powdery Mildew. No chlorosis observed even though Fortyniner is a parent. Necrotic spots, tip dieback, stem rot and root rot have not been observed.

Flowering description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (12–17 mm) will continue for two months or more. Individual flowers last two weeks or more after opening. No perceived fragrance.

(B) *Flowering response.*—Flowering time under controlled daylength after start of short days is 11 weeks in summer to 13 weeks in winter. Requires positive short days, 14½ hour nights for 42 consecutive nights for uniform induction of flowers.

(C) *Flowers borne.*—Compound dichasial cymes; peduncle length 5–15 cm, diameter 4–8 mm; pedicel length 5–7 mm, diameter greater than 1 mm.

(D) *Quantity of flowers.*—Very floriferous; floral count 80–100 per primary inflorescence, 400–500 total per 10 cm pot plant, commercial culture.

(E) *Petals.*—1. Shape: Slightly pointed to almost round. 2. Color: Upper surface: Closest to 8A to 8B. Under surface: Closest to 8C. 3. Number of petals: 4, united in corolla. 4. Flower diameter: 15 to 17 mm at maturity.

(F) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, cyrstalline, color greenish white. b. Style color: Light green. c. Ovaries: 4-celled, color light green.

(G) *Flower diseases.*—Resistant to Botrytis; no color breaking and little fading.

I claim:

1. A new and distinct Kalanchoe plant named Sparkler, as described and illustrated.

* * * * *

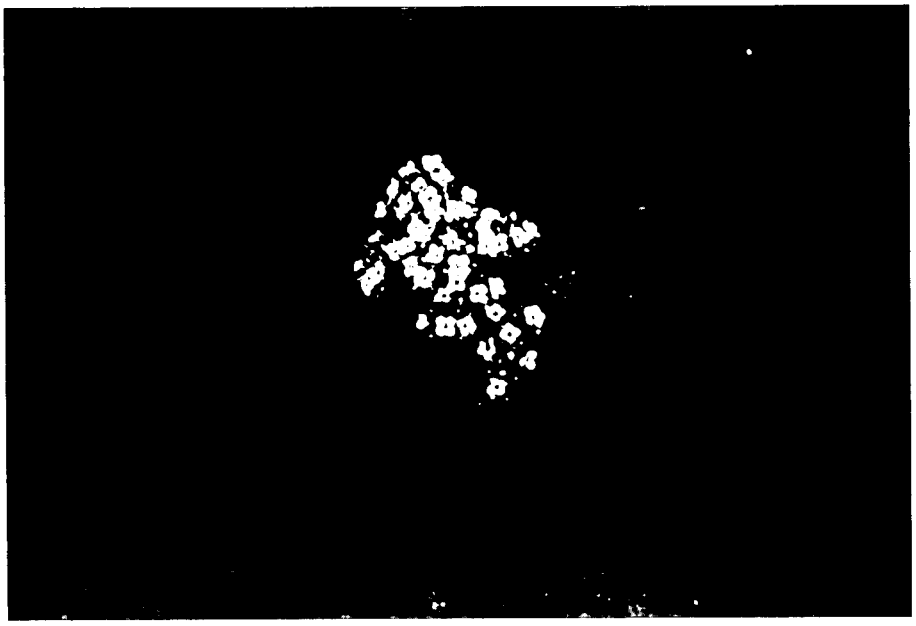

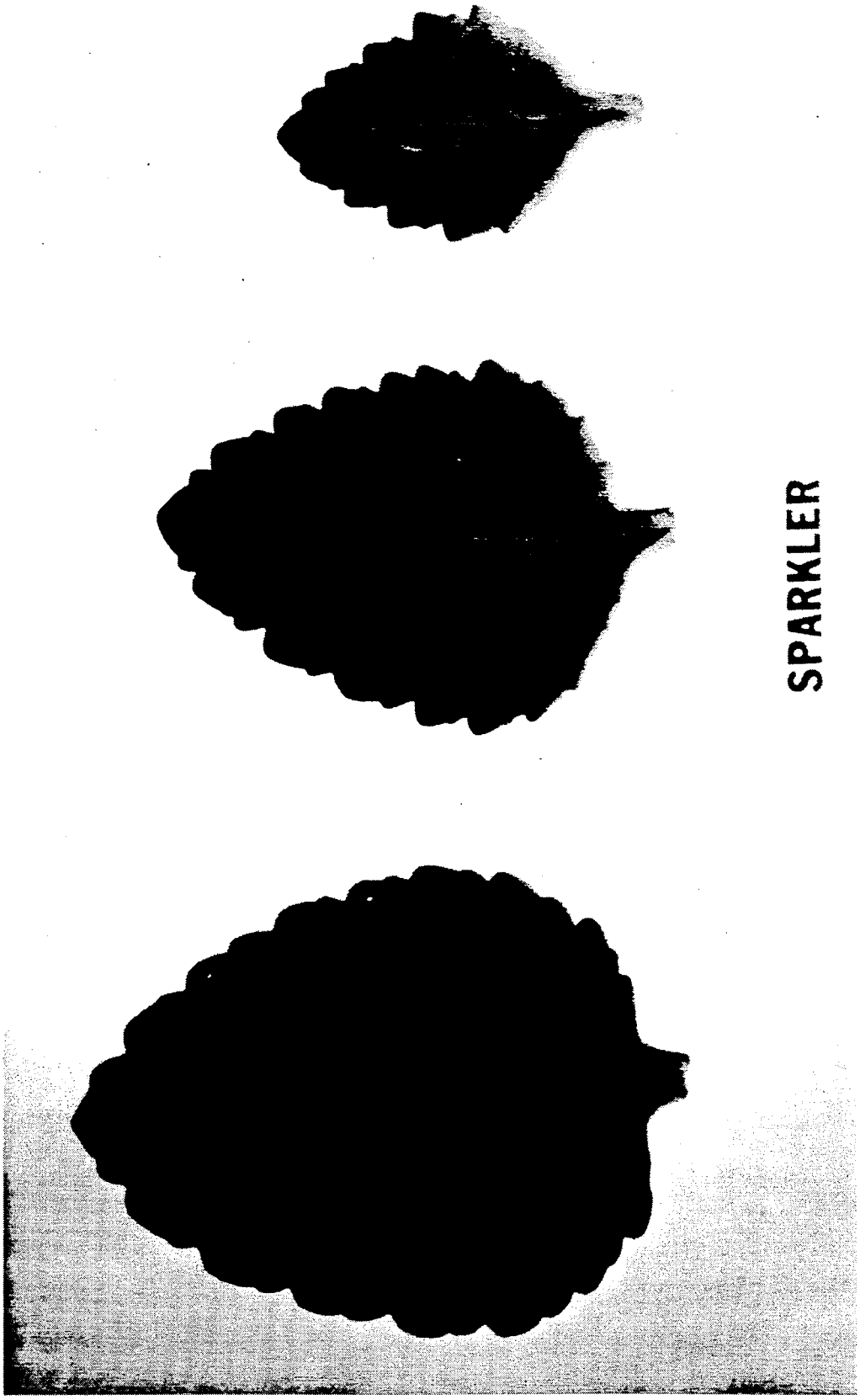
SPARKLER